(12) United States Patent
Brandt

(10) Patent No.: US 10,197,484 B2
(45) Date of Patent: Feb. 5, 2019

(54) DEVICE AND METHOD TO MEASURE THE EFFECTIVENESS OF PROTECTIVE SPORTS EQUIPMENT

(71) Applicant: Richard A. Brandt, New York, NY (US)

(72) Inventor: Richard A. Brandt, New York, NY (US)

( * ) Notice: Subject to any disclaimer, the term of this patent is extended or adjusted under 35 U.S.C. 154(b) by 184 days.

(21) Appl. No.: 15/043,111

(22) Filed: Feb. 12, 2016

(65) Prior Publication Data

US 2016/0279502 A1 Sep. 29, 2016

Related U.S. Application Data

(60) Provisional application No. 62/139,174, filed on Mar. 27, 2015.

(51) Int. Cl.
*G01N 3/30* (2006.01)
*G01N 3/303* (2006.01)
(Continued)

(52) U.S. Cl.
CPC .............. *G01N 3/30* (2013.01); *G01N 3/303* (2013.01); *A63B 71/10* (2013.01);
(Continued)

(58) Field of Classification Search
CPC ....................................................... G01N 3/30
See application file for complete search history.

(56) References Cited

U.S. PATENT DOCUMENTS

| 161,737 A | * | 4/1875 | Beardslee | ................ G01N 3/30 |
| | | | | 73/12.13 |
| 2004/0074283 A1 | * | 4/2004 | Withnall | ................. G01N 3/32 |
| | | | | 73/12.12 |

(Continued)

OTHER PUBLICATIONS

Manoogian, Head Acceleration is Less Than 10 Percent of Helmet Acceleration During a Football Impact, ISB XXth Congress—ASB 29th Annual Meeting, 2005.*

(Continued)

*Primary Examiner* — Manish S Shah
*Assistant Examiner* — Timothy Graves
(74) *Attorney, Agent, or Firm* — R. Neil Sudol; Henry D. Coleman

(57) ABSTRACT

This patent describes devices and methods to evaluate and compare the effectiveness of protective equipment in providing protection to players of contact sports, and to determine if a given protective product (pad) is compliant with a specified performance standard. To simulate the impacts experienced by these players, a pad-protected specially modified and instrumented manikin is impacted with solid loads of various weights at various speeds. The impacts are designed to model the impact forces and impact times encountered in typical game collisions. For each impact, measurements are made of the force exerted onto the pad, and the parts of this force that are transmitted through the pad onto various locations on the manikin, as a function of time. Five numbers that quantify the ability of each pad to protect the user are extracted from these measured force verses time data: (1) the maximum force applied on the pad, (2) the average applied force, (3) the maximum force measured under the pad, (4) the sum of the maximum forces measured under the pad, and (5) the ratio of the rebound load speed and the incident load speed. For a given impact, the (Continued)

pad that reduces the magnitudes of these quantities the most is the pad that provides the greatest measure of safety for the game players.

22 Claims, 8 Drawing Sheets

(51) Int. Cl.
    *G01L 5/00*     (2006.01)
    *F41H 1/00*     (2006.01)
    *A63B 71/10*     (2006.01)
    *G09B 23/30*     (2006.01)
    *A63B 71/12*     (2006.01)
(52) U.S. Cl.
    CPC ............ *A63B 71/1225* (2013.01); *F41H 1/00* (2013.01); *G01L 5/0052* (2013.01); *G09B 23/30* (2013.01)

(56) References Cited

U.S. PATENT DOCUMENTS

2009/0288472 A1* 11/2009 Le Carpentier ......... F41A 31/00
    73/12.04
2012/0330599 A1* 12/2012 Roberts .............. G01R 33/0064
    702/150

OTHER PUBLICATIONS

Cripton, Bicycle helmets are highly effective at preventing head injury during head impact: Head-form accelerations and injury criteria for helmeted and unhelmeted impacts, Accident Analysis and Prevention, 2014.*
Walsh, Dynamic impact response characteristics of a helmeted Hybrid III headform using a centric and non-centric impact Protocol, Journal of Sports Engineering and Technology, 2012.*
TQC Impact Tester, YouTube, Mar. 25, 2011, https://www.youtube.com/watch?v=wEjd68lzM_8.*
TQC Impact Tester Manual.*

* cited by examiner

DEVICE AND METHOD TO MEASURE THE EFFECTIVENESS OF PROTECTIVE SPORTS EQUIPMENT

BACKGROUND OF THE INVENTION

The present invention relates an apparatus for evaluating effectiveness of protective sports equipment such as shoulder pads, shin guards and helmets.

Protective equipment products, such as shoulder pads and helmets, are used in many contact sports in order to reduce the risk of injury to the players involved. Such injuries can be extremely severe, leading to serious physical and mental injuries and even to death. It is therefore very important to be able to measure and compare the effectiveness of a given protective product in providing the desired protection.

OBJECTS OF THE INVENTION

It is an object of the invention to provide a method and associated apparatus for measuring or testing the effectiveness of protective sports equipment such as shoulder pads, chest pads, shin guards, helmets, etc.

A related object of the present invention is to provide such a method and/or associated apparatus that is easy to use.

A further object of the present invention is to provide such a method and/or associated apparatus that is readily utilizable in enforcing safety standards practices.

These and other objects of the present invention will be apparent from the drawings and descriptions herein. It is to be noted that any single embodiment of the invention may not achieve all of the objects of the invention, but that every object is attained by at least one embodiment.

SUMMARY OF THE INVENTION

A method for measuring effectiveness of protective sports devices comprises, in accordance with the present invention, placing a protective sports device on a manikin part so as to simulate a person's use of the protective sports device, operating a projectile apparatus to at least indirectly impact the protective sports device at a predetermined location on the device and concomitantly over the manikin part with a projectile of predetermined mass having a predetermined or prescribed velocity, and, during the impacting of the projectile on the protective sports device, operating one or more sensors to measure respective accelerations or, equivalently, forces exerted by the impact on at least one of the protective sports device and the manikin part.

The one or more sensors are positioned to measure forces/accelerations at locations on an upper or outer surface of the protective sports device, at or near a point of impact of the projectile upon the protective sports device, or between the protective sports device and the manikin part. A sensor for measuring the impact force of the projectile upon the protective sports device may take the form of an accelerometer attached to the impacting projectile. Preferably, at least one of the sensors is placed at a predetermined position between the protective sports device and the manikin part.

The method may further comprise connecting the one or more sensors to an electronic signal processor and operating the signal processor to record and compute at least one measure of effectiveness of the protective sports device, the measure being computed in accordance with an algorithm taken from the group:

(i) an algorithm determining the maximum recorded acceleration and force;

$$SI = \int_0^{t0} a(t)^p dt \quad \text{(ii)}$$

where SI, standing for "Severity Index," is the integral of acceleration a(t) of the impacting projectile, raised to power p, over the duration of the impact and where a(t) is the acceleration (in g's) recorded on an accelerometer attached to the impacting weight w, at time t during the impact, and where f(t)=w*a(t) is the corresponding force;

$$(1/T) \times \int_0^T f(t) dt \quad \text{(iii)}$$

which represents an average of the applied force f(t) over the duration T of the impact;

(iv) an algorithm determining the maximum and average forces measured on each sensor under the pad, (v) an algorithm determining the sum of the maximum and average forces measured on each sensor under the pad; and (vi) the ratio e=v'/v of the rebound load speed v' and the incident load speed v.

The method may additionally comprise positioning an elastic member on the protective sports device at the predetermined location of impact. Then the operating of the projectile device includes directing the projectile to impact the protective sports device via the elastic member. An alternative method may comprise attaching an elastic member to the projectile. In either case the elastic member is located between the protective sports device and the projectile at the time of impact.

The projectile apparatus preferably takes the form of a weight dropping apparatus, so that the operating of the projectile apparatus includes releasing the projectile from a predetermined height above the protective sports device and the manikin part.

Specifically, an assembly for measuring effectiveness of protective sports devices may comprise, in accordance with the present invention, a frame; a rod or rail supported by the frame in an at least partially vertical orientation; a mass or weight (the projectile) slidably (preferably with minimal friction) mounted to the rod or rail; and an elastic member disposed at a lower end of the rod or rail. The rail or guide is positioned to terminate at or proximate the predetermined location on the protective sports device. The operating of the projectile device concomitantly includes directing the projectile to the predetermined location via the rail or guide.

The assembly may also comprise a manikin part for temporary attachment to a protective sports device in simulation of a user's wearing the protective sports device, wherein the elastic member is positionable at a predetermined location on the protective sports device over the manikin part for receiving the mass or weight during an impact of the mass or weight on the protective sports device. The manikin part may consist of a hard polymeric shell surrounding a more resilient polymeric filling material.

Pursuant to another feature of the present invention, the assembly further comprises a holder having a recess. The holder is disposable on the protective sports device at the predetermined location in order to transmit an applied force to the device. The elastic member has a lower end positionable inside the recess.

The assembly may additionally include at least one force sensor disposable at a location taken from the group consisting of an upper surface of the protective sports device, at or near a point of impact of the projectile upon the protective sports device, and between the protective sports device and the manikin part. The at least one sensor may be attached to the projectile.

Preferably the assembly includes a plurality of force sensors each disposable at a location taken from the group consisting of an upper surface of the protective sports device, at or near a point of impact of the projectile upon the protective sports device, and between the protective sports device and the manikin part. Preferably, an electronic signal processor is operatively connected to the sensors and configured to record output signals of the sensors (for instance, encoding acceleration) as functions of time. The signal processor is preferably configured to compute at least one measure of effectiveness of the protective sports device in response to the signals from the sensors(s). The measure may be computed in accordance with one or more of the following algorithms:

(i) an algorithm determining a maximum recorded acceleration and force;

$$SI = \int_0^{t0} a(t)^p dt \quad \text{(ii)}$$

where SI, standing for "Severity Index," is the integral of acceleration a(t) of the impacting projectile, raised to power p, over the duration of the impact and where a(t) is acceleration as recorded on an accelerometer attached to the impacting weight w, at time t during the impact, and where f(t)=w*a(t) is the corresponding force;

$$(1/T) \times \int_0^T f(t) dt \quad \text{(iii)}$$

which represents an average of the applied force f(t) over the duration T of the impact;

(iv) an algorithm determining maximum and average forces measured on each sensor under the pad;

(v) an algorithm determining the sum of the maximum forces measured on each sensor under the pad; and (vi) the ratio e=v'/v of the rebound load speed v' and the incident load speed v.

The elastic member may take the form of a helical spring, which has a lower end positioned inside the recess and an upper end surrounding a lower end portion of the rod or rail.

BRIEF DESCRIPTION OF THE DRAWINGS

FIG. 5b is a top plan view of a spring included in the pad testing apparatus or assembly of FIG. 5a.

FIG. 5d is a tope plan view of a cup element or spring holder included in the pad testing apparatus or assembly of FIG. 5a.

FIG. 5e is a side elevational view of the cup element or spring holder of FIGS. 5d and 5a.

DETAILED DESCRIPTION

While the football shoulder pad will be referred to as the protective equipment being tested pursuant to the invention, in it is to be understood that the same inventive equipment and analysis applies to other protective products such as helmets, shin guards, chest guards, etc., used in various contact sports.

There are three principle ways in which a shoulder pad can lessen the internal bodily damage caused by the impact from an external body.

(1) The force applied to a shoulder by the external body can be reduced because of the dissipation of kinetic energy (mainly into thermal energy) within the pad as the force is applied.

(2) The severity of the impact can be reduced by the pad because of the pad's ability to decrease the size of the applied force and control the time over which it acts.

(3) The pad can spread the total transmitted force over an area that is larger than the area over which the applied force acts.

These statements are explained in detail below.

Figure 1:
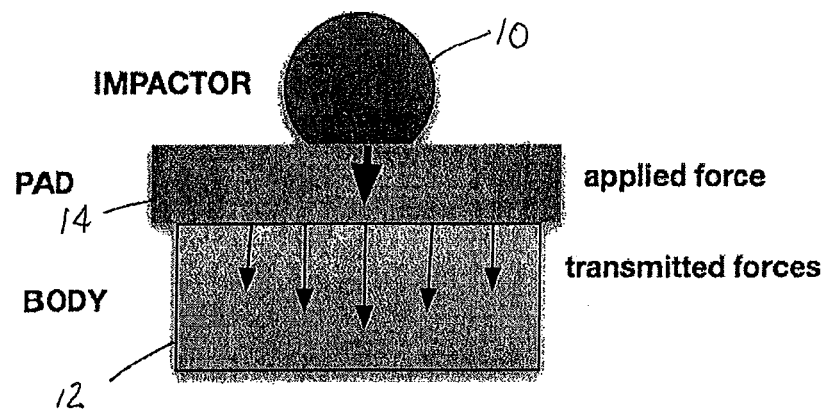
FIG. 1 is a diagram showing the distribution of forces during impact of a projectile body with a protective sports device such as a pad.

(1) As depicted in FIG. 1, when an external projectile body 10 of weight w (mass m=w/g, where g is the acceleration of gravity) impacts, with a speed v, a body 12 protected by a pad 14, the projectile body 10 exerts a force f(t) on the pad 14 at all times t during the impact. (Choosing t=0 at the start of the impact, let t0 denote the time that the impact ends, and call t0=T the "impact time".) It is important to recognize that this exerted force f(t) is transmitted undiminished through the pad 14 onto the internal body. (See FIG. 1) The pad 14 cannot reduce this force once it is applied, but it can reduce the force that is actually applied to begin with. If the pad 14 incorporates a dissipative material, the external projectile body 10 will rebound off of the pad 14 with a relative speed v' that is less than the incident speed v. The ratio of these speeds, e=v'/v, is called the "coefficient of restitution" (COR) between the two bodies 10 and 12/14, because it is the fraction of the incident speed that is restored after the impact. When e<1, the kinetic energy of the rebounding projectile body 10, $mv'^2/2$, is less than the kinetic energy $mv^2/2$ of the incident projectile body 10. In this case, some of the kinetic energy is transformed into thermal energy (heat) within the pad 14. The smaller is the COR, the more kinetic energy is so transformed, and the smaller is the force f(t) exerted on the pad 14 and on the protected body 12.

(2) The damping mechanism described in (1) above reduces the applied force f(t) at a range of times t during the impact (0≤t≤t0), but if this reduced force acts over a larger impact time t0, the impact can impart greater damage. It is therefore important that the pad does not increase the impact time to a degree that nullifies the effect of the reduction in the applied force. An accepted measure of the damage caused by an impact is the Severity Index (SI). The SI is the integral of the acceleration a(t) of the impacting body, raised to an appropriate power p, over the duration of the impact:

$$SI = \int_0^{t0} a(t)^p dt$$

Figure 2:
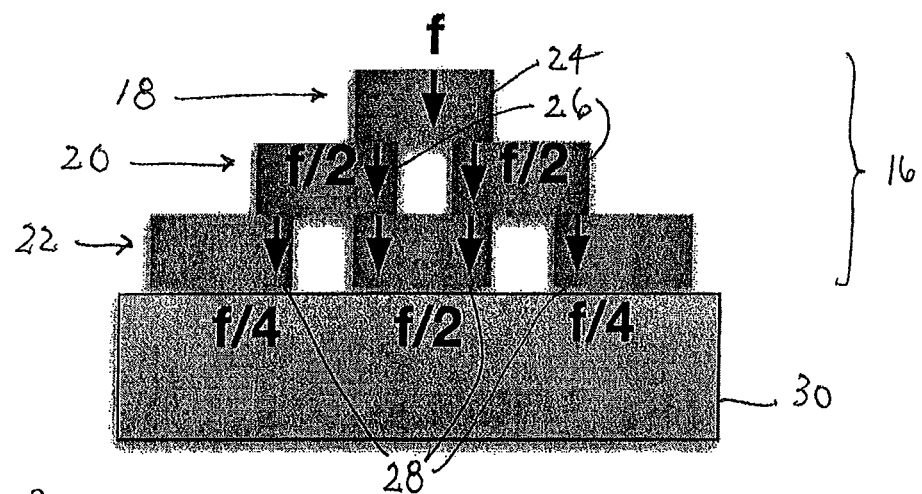
FIG. 2 is a diagram similar to FIG. 1, showing the distribution of forces during impact of a projectile body with a multi-layered protective pad.

In this expression, the acceleration a(t) is expressed in units of g, so it is dimensionless (a=f/w), and the time t is in seconds. For impacts to the head, the Gadd SI, in which p=2.5, is commonly used. There is no current SI in place for shoulder pad safety issues, so the same p=2.5 will be used here for comparative purposes. The smaller the SI, the less will be the bodily damage caused by the impact. An effective shoulder pad must significantly reduce the SI (3) The third way in which a shoulder pad can help protect an impacted body is by spreading the applied force over a relatively large area. The result of such a spreading is that the force applied to a given area of the internal body will be less than the net force applied on the pad. The total force transmitted to the body will be the same as the force applied on the pad, but the effective force felt will be less. In other words, the pressure (force per unit area) applied to the body will be less that the pressure applied to the pad. A pad can give rise to this spreading in a variety of ways because of its elastic and geometric properties. A simplified illustration of one such way is provided in FIG. 2. A pad 16 is divided into separate layers 18, 20, and 22 of elastic sections 24, 24 and 28. (For simplicity, only six sections 24, 26, and 28 and three layers 18, 20, and 22 are depicted.) A force f is applied to the top of the section 24 in the first level or layer 18. This force is transmitted onto the two sections 26 in the second level or layer 20. These sections 26 then transmit the f/2 forces (equally, for simplicity) to the three sections 28 in the third level or layer 22. Finally, these sections 22 transmit their acquired forces onto an underlying body 30 that is the subject of impact protection. The forces applied on three locations on the body 30 have been reduced to f/4 at the outer locations and f/2 at the central location. This illustration is, of course, highly simplified, but it shows how a well-designed pad 16 can protect areas of a target body 30 by reducing the pressure applied to them.

Figure 3:
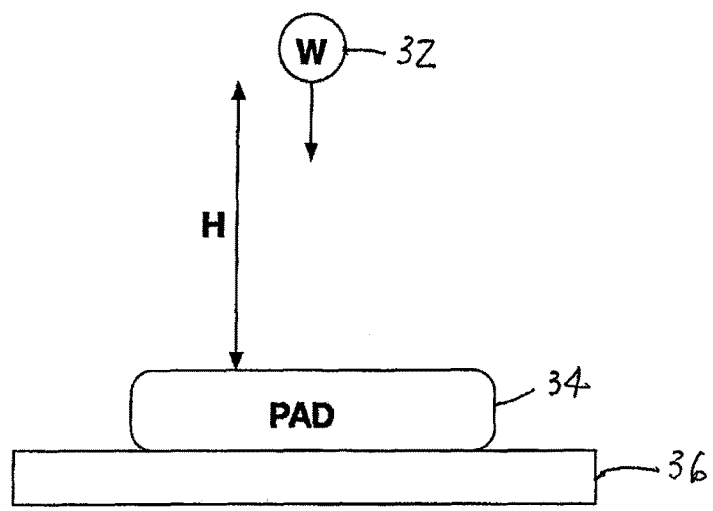
FIG. 3 is a diagram of a general pad testing method in accordance with the present invention.

The present disclosure elucidates simulation and measurement of the forces exerted on a pad-protected contact-sport player, and how to use the measured forces to evaluate and compare the protective capabilities of tested pads 34 (FIGS. 3-5a). In a simulation, a pad-protected body 36 in the form of a manikin is impacted with solid loads (projectiles 32) of various weights at various speeds. The force exerted on the manikin 36 by a projectile or weight 32 during the impact is measured by a sensor 38 such as an accelerometer attached to the weight, and the forces transmitted through the pad 34 onto the manikin 36 are measured at various locations by force sensors 40 (FIG. 7) attached to the manikin under the pad. The simplest possibility of a free falling projectile weight 32 impacting a target is illustrated in FIG. 3.

Figure 4:
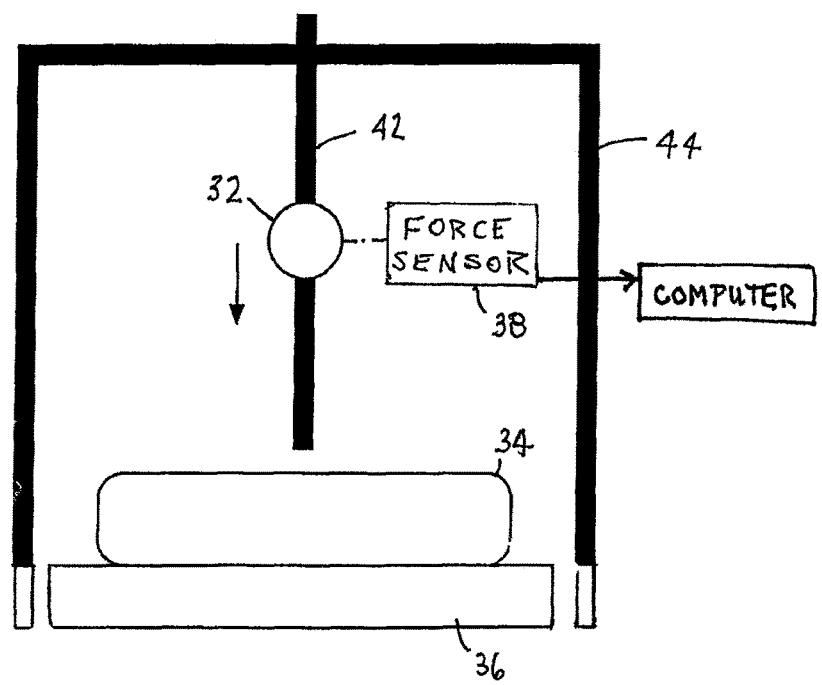
FIG. 4 is a diagram of an embodiment of a pad testing apparatus of assembly for carrying out the method of FIG. 3.
Figure 5A:
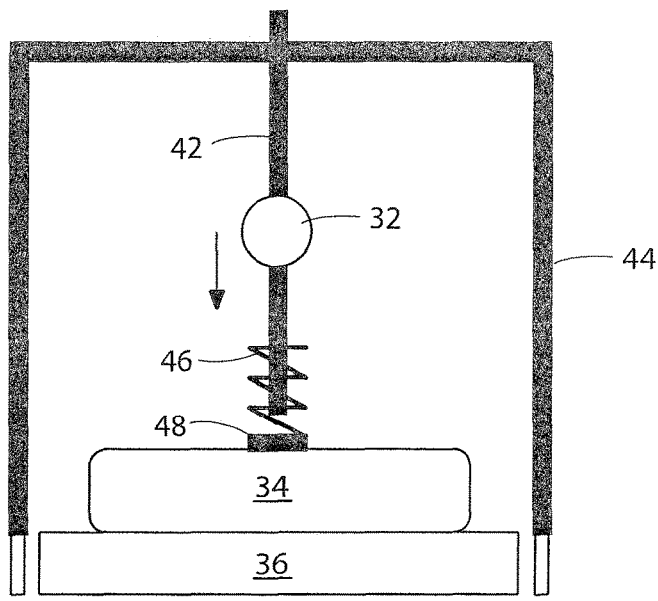
FIG. 5a is a diagram similar to FIG. 4, showing a further embodiment of a pad testing apparatus of assembly for carrying out the method of FIG. 3.
Figure 5B:
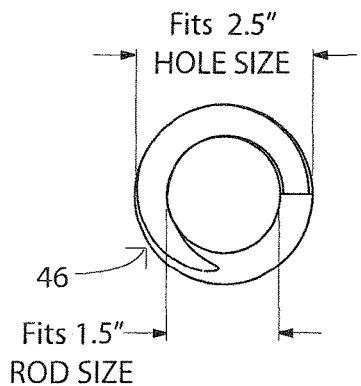
Figure 5C:
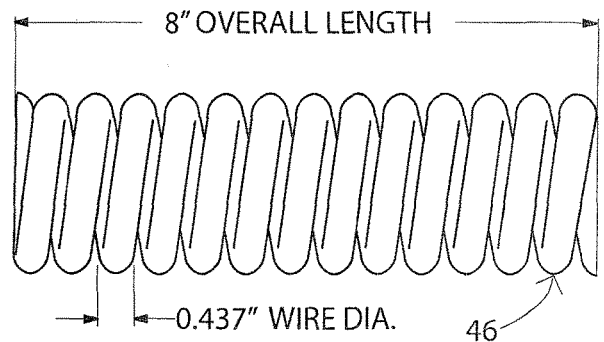
FIG. 5c is a side elevational view of the spring of FIG. 5b.

A preferred method to control the drop height, which determines the impact speed, the aim, which determines the impact point, and the rebound, is to have the loads slide down a lubricated vertical rod or rail 42 (see FIGS. 4 and 5a). Rod or rail 42 is supported by a frame 44 which may take any form, such as an A-frame or even a housing structure 44 (see FIG. 8). The rod or rail 42 enables the impact to be accurately aimed and controlled.

Figure 5D:
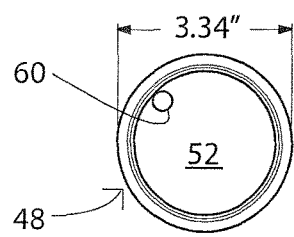
Figure 5E:
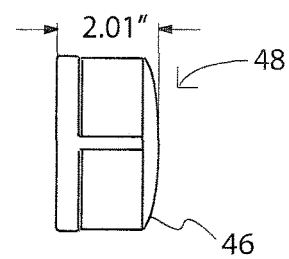
Figure 5F:
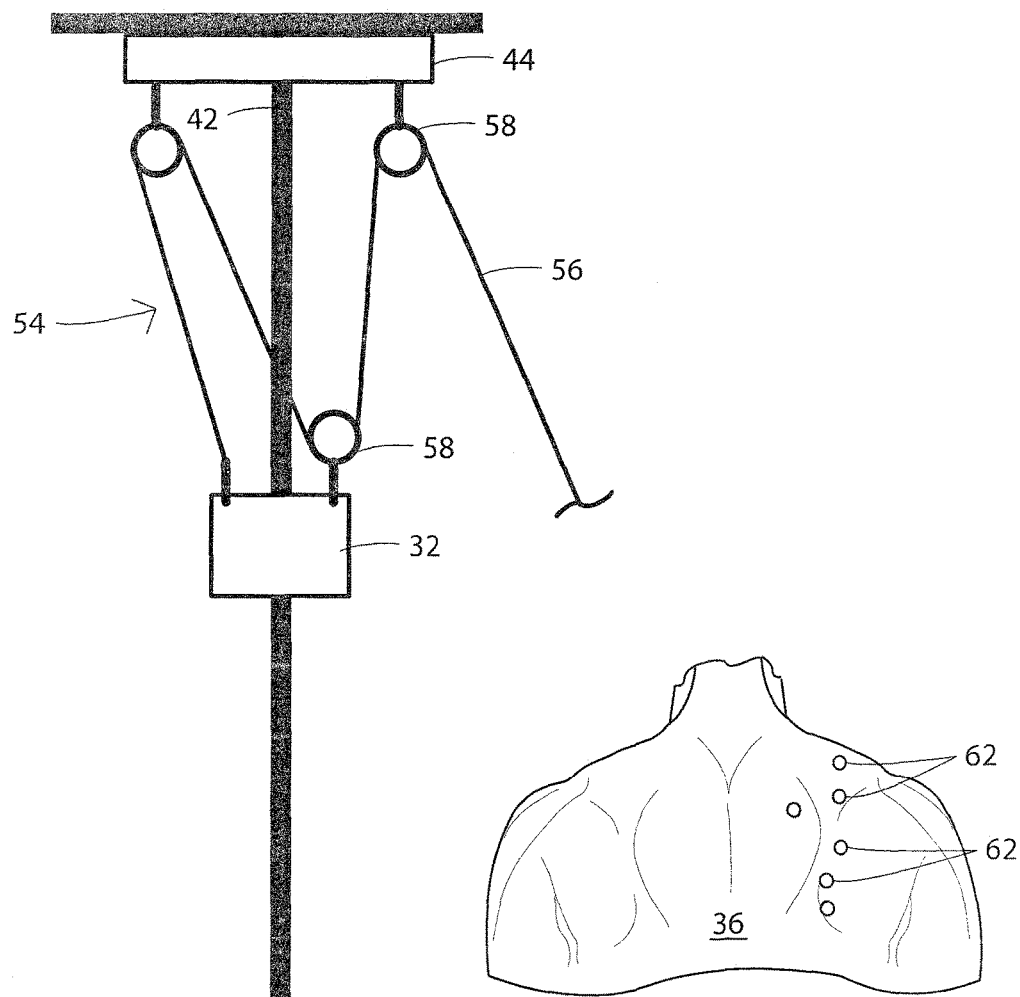
FIG. 5f is a schematic side elevational view of a particular embodiment of a pad testing apparatus or assembly for carrying out the method of FIG. 3.

As depicted schematically in FIG. 5a, an important additional inventive preferred embodiment is to have the falling load or projectile 32 strike a stiff helical spring 46 (or equivalent elastic member) attached to a solid cup-like holder 48 resting on pad 34. As shown in FIGS. 5d and 5e, cup 48 has a rounded bottom 50 that engages the pad 34 and distributes the impact force onto the pad, and an interior well 52 that accommodates a bottom part (not separately designated) of spring 46. The action of projectile or falling weight 32 in cooperation with spring 46 and cup 48 is designed to model typical game impacts with regard to impact force and impact time. (The direct impact of a solid load onto a pad, with no elastic interface, will produce an impact that is not a realistic simulation of impacts that occur in practice.) As shown in FIG. 5f, guide rod or rail 42 is attached to frame or support 44 from above, a bottom part of rod 42 is inserted into a top part of spring 46, a bottom part of spring 46 is seated in the well or recess 52 of cup 48, and an arrangement 54 of a rope 56 and pulleys 58 is used to raise the projectile load 32 to a predetermined desired height. This is an effective system, but there are obviously many other ways to support the rod, spring, and cup, and to lift and release the weight. One such alternative method consists of attaching the spring to the bottom of the projectile.

Preferably force measurements are made in at least three different locations and are recorded at periodic intervals for each impact. The first recorded measurement on each drop uses accelerometer 38 (FIG. 4) attached to the falling projectile or weight 32 to measure the acceleration verses time profile of the impact. The acceleration a(t) is measured in g's, so that the applied force is f(t)=w*a(t). The recorded data are used to evaluate the important aspects of this applied force profile. A second force sensor 60 may be located between the spring 46 and the retaining cup 48. Use of a force sensor attached there is an equivalent way to measure f(t).

Figure 6:
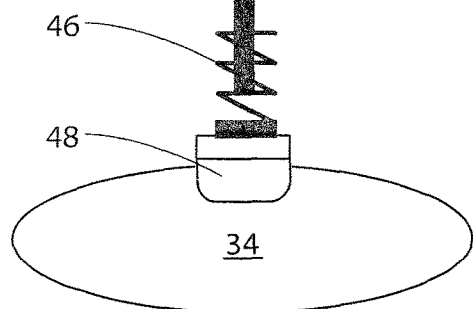
FIG. 6 is a front elevational view of a manikin part utilizable in testing a shoulder pad in accordance with the method of FIG. 3.
Figure 7:
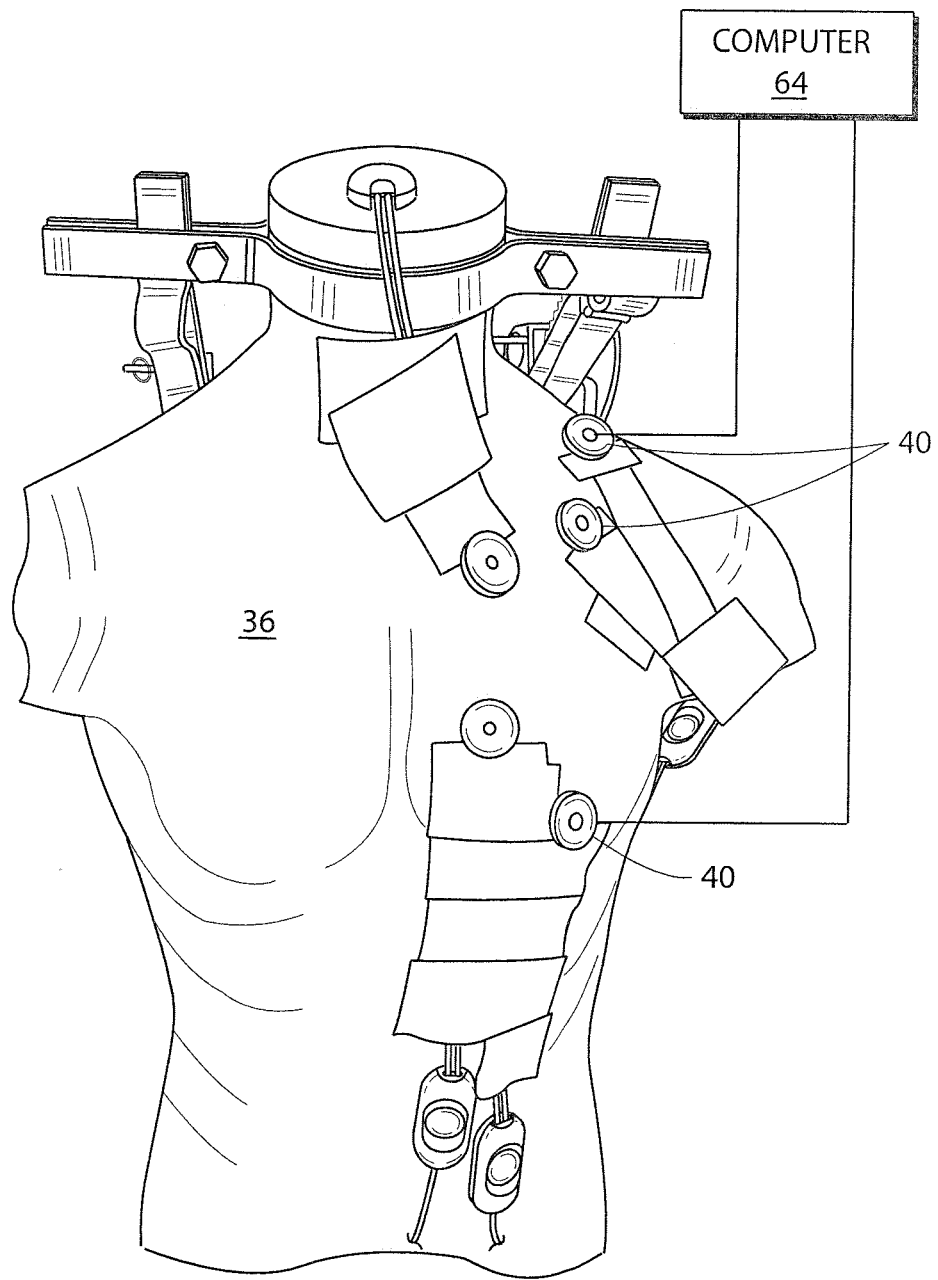
FIG. 7 is a front elevational view, on a smaller scale, of the manikin part of FIG. 6, showing force sensors attached to the manikin part.

A third measurement location is between pad 34 and manikin 36. The actual forces transmitted through pad 34 onto manikin 36 are recorded via force sensors 40 (FIG. 7) attached to a surface of the manikin. These forces are recorded at several separate locations 62 on the manikin (FIG. 6), in order to determine the degree to which a pad 34 is effective in spreading out the applied impact force. Force sensors 40 are attached to manikin 36 at one or more locations 62, as shown in FIG. 7. The outputs from these sensors 40 are recorded by a computer or microprocessor 64 and converted into force verses time spreadsheets or plots (see FIGS. 9-12) and are used to evaluate various performance metrics.

Figure 8:
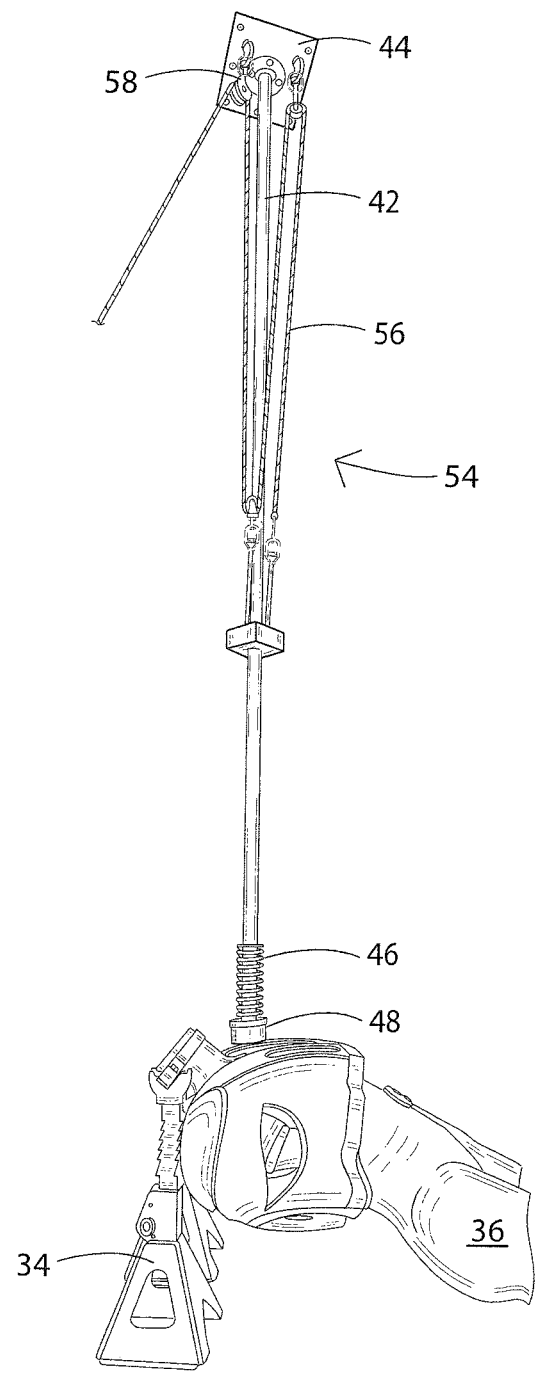
FIG. 8 is a perspective view of another particular embodiment of a pad testing apparatus or assembly for carrying out the method of FIG. 3.

For the testing of shoulder pads 34, manikin 36 is preferably made with a shell of a hard thick plastic material that is shaped like a human torso and is filled with a dense solid polymeric, for instance, polyurethane foam. The result is a suitable target that can withstand the 600 lb forces that are impacted upon it. (Similar body-models can be used for the testing of other protective equipment such as helmets and shin guards.) The weight of projectile 32 (about 25 lbs), impact speed (about 14 mph), and properties or spring 46 are chosen so that the force applied to manikin 36 (about 600 lbs) and the impact duration (about 0.05 s) are of the order of those encountered in actual game impacts. With these loads and impact speeds, the degree of force reduction provided by the elastic and damping properties of the pad 34 can be evaluated and compared. A complete operational system is shown in FIG. 8.

In order to compare the protective abilities of different shoulder pads, it is necessary to impact each pad in the identical way. With the apparatus described herein, this means that the impacts must arise from the same load weight w dropped onto the pads from the same height h; i.e., impacted at the same initial speed v. Since the friction between the loads and pole is very small, to a good approximation v and h are related by $v=\sqrt{(2\ gh)}$, where $g=32\ ft/s^2$ is the acceleration of gravity. The small correction from friction is determined by analyzing high-speed videos of the falling weight.

During the collision between a pad and the impacting load or projectile, the pad material is compressed and decompressed a number of times, and during these oscillations the pad material absorbs and releases elastic and thermal energy. The elastic energy is largely returned to the load and the thermal energy is largely dissipated as heat. The more of the incident load kinetic energy $mv^2/2$ (m=w/g) that is transferred into thermal energy, the smaller will be the force exerted by the load on the pad, and the smaller will be the (equal and opposite) force exerted by the pad on the load. If v' is the rebound speed of the load immediately after the impact, then $mv^2/2-mv'^2/2$ is the kinetic energy of the load that is lost during the impact. The larger this kinetic energy loss, the greater the heat produced, and the better the protection provided by the pad.

To obtain the force data necessary to quantify the protective performance of a given pad, and to compare different pads, each pad must be impacted in exactly the same way. This means that the incident load weight w and drop height h must be the same. From these data, the following most relevant information is extracted: (1) the maximum force applied on the pad, (2) the average applied force, $$(1/T) \times \int_0^T f(t)dt,$$

(3) the severity index $$\int_0^T a(t)^{2.5} dt,$$

(4) the maximum force measured on a sensor under the pad, (5) the sum of the maximum forces measured on each sensor under the pad, and (6) the ratio e=v'/v of the rebound load speed and the incident load speed.

The significance of this information is as follows. (1) The maximum applied force is a measure of the effectiveness of a pad in reducing the impact force. (2) The average applied force and the severity index are measures of the effectiveness of a pad in reducing the impact force and in spreading this force out over the impact time. They are measures of the severity of the impact, as described previously. (3) The maximum force measured on a sensor under the pad is a measure of how much of the applied force is transmitted through the pad onto the sensor. It is a measure of the effectiveness of a pad in spreading the applied force over the body of the player. (4) The sum of the maximum forces measured on each sensor under the pad is another measure of the effectiveness of a pad in spreading the applied force over the body of the player. If under-pad sensors were placed over the entire protected body of a player, then this sum would nearly equal the applied force. Because the under-pad sensors cover only a smaller (most relevant) area of the body, the force sum will be less than the applied force. (5) The speed ratio e=v'/v is called the "coefficient of restitution" (COR) between the load and the pad because it gives the fraction of the incident load speed that is restored to the load after the impact. It is a direct measure of the kinetic energy of the load that is lost during the impact: $mv^2/2-mv'^2/2=(mv^2)*(1-e^2)/2$.

The above six quantities together effectively characterize the ability of the measured pad to reduce the severity of an impact. For a given impact, the pad that reduces the magnitudes of these quantities the most is the pad that provides the greatest measure of safety for the football player. Because the preferred manikin impacts proceed through a stiff spring (which models the elasticity of a realistic impacting element), it is possible to measure the force exerted from an impact on a surface when no protective pad is in place. The difference between this force and the force exerted from an identical impact when a protective pad is present constitutes a direct measure of the effectiveness of the pad. This force difference, expressed as a percentage of the force exerted in the absence of a pad, will be referred to as the "impact reduction percentage (IRP)". For a given impact on a given pad, the larger the IRP, the greater is the protection provided by the pad. It is the elasticity of the spring used to transfer the force from the falling weight onto the pads that enables the inventive introduction of this new and more easily understood performance metric. Direct contact impacts without an elastic intermediary would produce forces too large and uncontrollable to provide a useful baseline.

Preferred values of the drop height (4'), the load weight (25 lb), and the spring parameters produce a maximum force of F0=620 lbs exerted on the manikin when no protective equipment is present. If F is the maximum force exerted by this impact when protective equipment is present, then the maximum-force-impact-reduction-percentage (IRP) of that equipment is

IRP=100*(F0−F)/F0.

Typical IRP values are given below. For the impacts on the manikin, the forces arising using three types of targets are given: (1) Impacts when no pad is present. These are used to provide the baseline for the IRP values. (2) Impacts when only a foam vest is present. These are used to provide information on how much of the protection from a pad comes from the vest alone (without the outer shell). (3) Impacts on complete pads. These are used to quantify the protection provided by the full pads.

To compare the effectiveness of the various objects impacted, some of the metrics introduced above will be used (maximum and average exerted forces, severity index, COR)

as well as the IRP values for these quantities. Values of these metrics for an effective tested pad are given in the following table. The pad in question is seen to reduce the maximum force by 22.7%, the average force by 29.7%, the COR by 50.4%, and the severity index by 57.1%.

| PAD EFFECTIVENESS METRICS | | | |
|---|---|---|---|
| METRIC | WO PAD | WITH PAD | IRP |
| max force | 594 | 459 | 22.7 |
| ave force | 330 | 232 | 29.7 |
| sev index | 88.3 | 37.9 | 57.1 |
| cor | 0.448 | 0.222 | 50.4 |

The metric values displayed above represent only a small part of the total data collected during each impact. All of the collected data used to determine the metric values for these impacts (usually over 4000 force measurements per impact) are displayed in force verses time graphs, some of which are shown in FIGS. 9-12.

Figure 9:
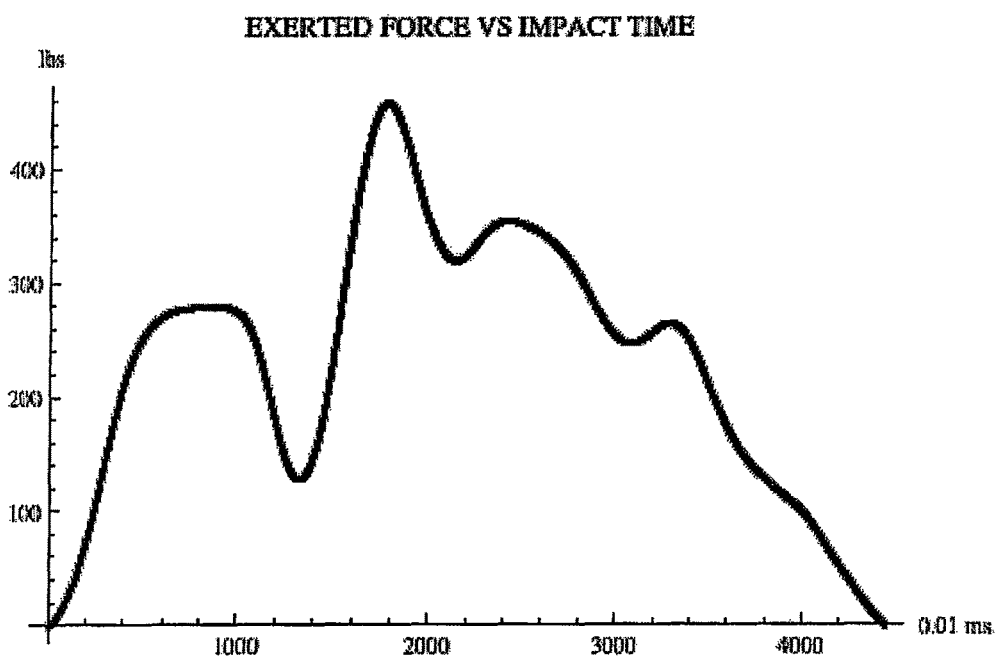
FIGS. 9-12 are graphs showing force as a function of time, per output signals of sensors as depicted in FIGS. 4 and 7.

A typical impact force verses time graph for a shoulder pad is shown in FIG. 9. The vertical axis specifies the measured force in pounds. The horizontal axis specifies the elapsed time during the impact in units of 0.01 ms. The accelerometer records 100,000 force measurements per second, so the time between measurements is 0.00001 s=0.01 ms. The total duration time of this impact is thus about 0.043 s, during which 4,300 measurements were made. The maximum measured force is 459 lbs. (The irrelevant high-frequency vibrations created by the impact were removed using a CFC60 filter.) The entire impact, with a duration of 0.043 sec, corresponds to an oscillation of the stiff spring used to model an impacting body. The superimposed higher frequency oscillations are created by the elasticity of the pad.

Figure 10:
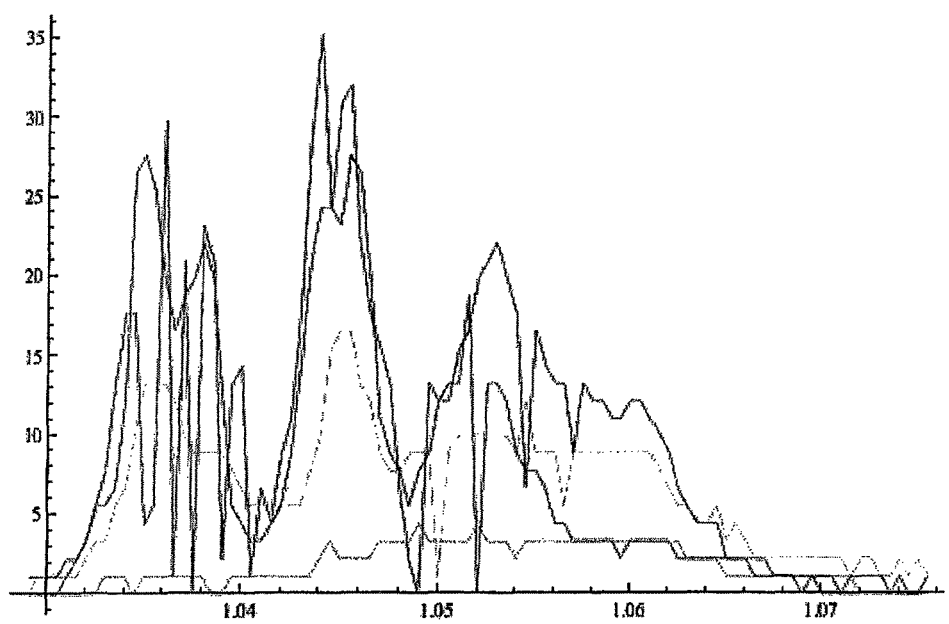
Figure 11:
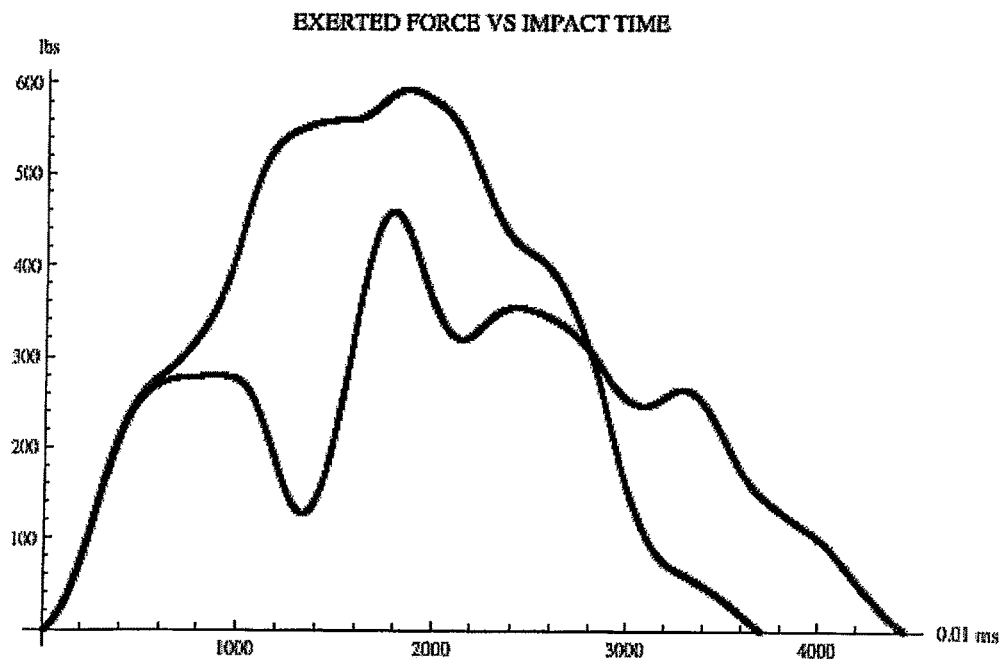

The forces measured on four of the sensors under the pad, near the impact area, are shown in FIG. 10. The vertical axis specifies the measured force in pounds, and the horizontal axis specifies the elapsed time during the impact in units of 0.01 s. The peak measured force on a sensor is about 36 lbs. The horizontal time units are 5 ms. The total peak force of the sum is about 80 lbs. The remainder of the 459 lb applied force occurs in areas on the manakin not monitored by these force sensors.

The baseline for the IRP evaluations is provided by the impact on the manakin when no protective material is in place. The graph of this impact, together with the previous graph of the pad-protected impact, is given in FIG. 11. The peak measured force without the pad is seen to be about 30% larger than the one with the pad, and the impact duration is about 15% shorter. The corresponding effectiveness metrics are given in the following table. This table demonstrates how the IRP is used to determine the degree to which a given pad reduces an applied force from a given impact. The first row of data gives the forces measured when no protection is present. The second row of data gives the forces measured when the protection is provided by a pad's inner foam vest alone, without the outer shell. The third row of data gives the forces measured when a complete pad is present. Column 1 lists the target, column 2 lists the value of the maximum measured force, column 3 lists the average measured force values, column 4 lists the measured COR values, columns 5-7 list the IRP values for the previous columns, column 8 lists the sum of the maximum forces measured under the targets, and column 9 lists the percentage of the column 2 forces measured in column 8. In columns 2, 3, and 4, smaller values correspond to greater protection, whereas in the IRP columns 5, 6, and 7, larger values correspond to greater protection.

| COMPARISON OF IMPACTS | | | | | | | | |
|---|---|---|---|---|---|---|---|---|
| TARGET | max f | ave f | cor | max f IRP | ave f IRP | cor IRP | sum under | under/ over % |
| none | 620 | 354 | 0.448 | 0.0 | 0.0 | 0.0 | | |
| vest | 493 | 255 | 0.318 | 20.5 | 27.8 | 29.0 | 134 | 27 |
| pad | 459 | 243 | 0.290 | 26.0 | 31.4 | 35.3 | 89 | 19 |

The force F0 measured when no pad is present serves as the baseline for the IRP values: IRP=100*(F0−F)/F0. The F0=620 lb maximum unprotected force is reduced to 493 lbs by the vest alone (20.5% reduction), and the F0=354 lb average unprotected force is reduced to 255 lbs by the vest alone (27.8% reduction).

Figure 12:
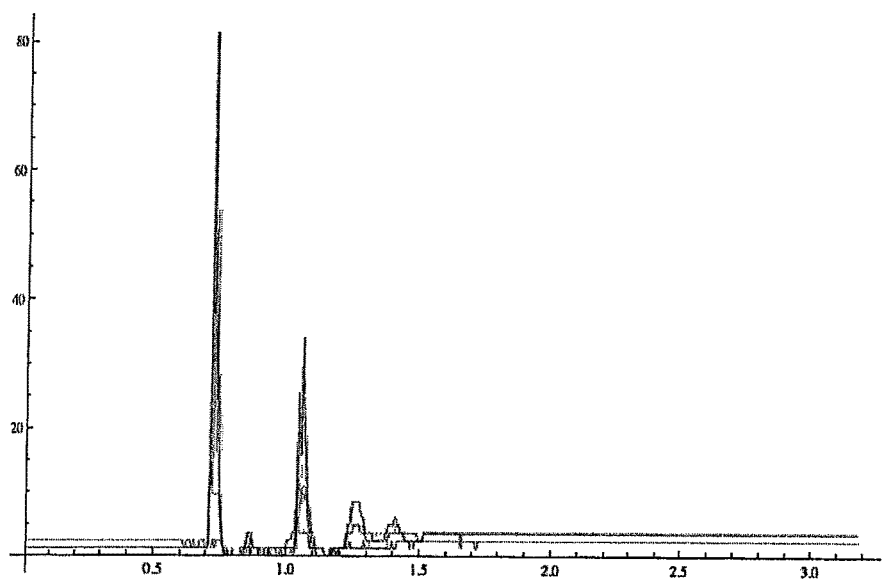

To determine the degree to which a pad spreads out the force applied on it, the force applied on each sensor under the pad is measured as a function of time. FIG. 12 displays the forces recorded on each of five sensors, after a load of 25 lbs is dropped from a height of 6 ft, with a different shade for each sensor. The largest recorded force during the first bounce of the load is 81.6 lbs. The forces exerted in subsequent bounces are seen to decrease because the loads bounce back up to a smaller height, because of the kinetic energy loss due to the damping effects within the struck pad. (The kinetic energy is transferred into thermal energy during the compressions of the pad.) The smaller the forces measured in the subsequent bounces, the better is the pad at reducing the size of the applied and transmitted forces. The total of the maximum forces exerted on each sensor is 157 lbs. The data relevant to the performance metrics are those recorded during the first bounce.

The performance metrics introduced above can be use to compare the effectiveness of different pads. The following table displays the results of identical impacts on three shoulder pads (labeled A,B,C) for relatively large applied forces. The forces were measured using a 25 lb load dropped from a height of 6 ft. The MAXIMUM APPLIED FORCE column gives the maximum of the force measured on top of the pads. The next column gives the average values of the applied forces over the impact durations. The MAXIMUM TRANSMITTED FORCE column gives the maximum force value recorded on a single sensor under the pad, and the SUM TRANSMITTED FORCE column gives the sum of the maximum values of the recorded forces on all five of the sensors under the pad. The COR column gives the coefficient of restitution between the impacting weight and the pad. As previously explained, these COR values are measures of the energy dissipated within the pad. (The smaller the COR, the more kinetic energy is transformed into heat.) The final column gives the percentage of the maximum applied force on top of the pad that is transmitted onto the five sensors distributed under the pad. For a given impact, the pad that reduces the magnitudes of these metrics the most is the pad that provides the greatest measure of safety for the football player. Pad A is seen to be superior in this case. The lower two rows give the percentage protective advantage of pad A compared to pad B and pad C.

PAD TESTING DATA SUMMARY

| TESTED PAD | MAX APP FORCE | AV APP FORCE | MAX TRN FORCE | SUM TRN FORCE | EN TFR COR | SUMTR/ MAXAP |
|---|---|---|---|---|---|---|
| A | 580.4 | 222.4 | 59.5 | 85.9 | 0.293 | 0.15 |
| B | 632.6 | 276.0 | 83.7 | 163.1 | 0.397 | 0.26 |
| C | 609.9 | 251.6 | 94.8 | 138.8 | 0.326 | 0.23 |
| A/B % | 9.0 | 24.1 | 40.7 | 89.9 | 35.5 | 20.0 |
| A/C % | 5.1 | 13.1 | 59.3 | 61.6 | 11.3 | 74.0 |

A performance standard for shoulder pads can be based on measurements such as those described above. For example, the maximum applied force for a given drop (say a 25 lb drop from 6') can be limited to a chosen value (say to 610 lbs, in which case pads A and C would be compliant, but not pad B.)

In addition to such testing of new pads, durability issues can also be addressed. It is possible that the protective qualities of a pad will deteriorate over time from the cumulative effects of multiple impacts. This effect can be investigated by re-measuring the applied and transmitted forces after subjecting pads to multiple impacts.

The measurement equipment and data analysis described above were very specific, but the concepts taught here are much more general. The inventive aspects, and their possible generalizations, can be summarized as follows.

1. The impact method, in which a given weight slides down a vertical rod, from a given height, aimed at a given impact location on the given pad, can be changed. What is important is that the impacts used to compare the effectiveness of different pads involve identical weights and speeds that strike the pad as free bodies through identical interfaces at the chosen location. Alternative impact mechanisms, such as shooting the impacting weights from an air cannon, can be used, as long as the stated conditions are satisfied.
2. The equipment used to measure the applied and transmitted forces can be changed. A variety of force and acceleration measurement devices are available can be used as long as they are sufficiently accurate and robust.
3. The six performance metrics introduced here are: maximum applied force, average applied force, severity index, maximum transmitted force, total transmitted force (on chosen sensor locations), COR, and local transmission percentage. The IRP values corresponding to these metrics have also been introduced. Alternative metrics, such as other suitably defined severity indices, can be used, as long as they are shown to be relevant to injury occurrence.
4. In the analysis of the directly measured data consisting of force and acceleration values as functions of impact time, original computer software was written that used these data to evaluate the above performance metrics. Other programs can be used as long as they can perform the necessary evaluations accurately and efficiently.
5. The performance metrics defined above can be used to implement a safety standard by requiring that a compliant pad produces values of one or more of these metrics that do not exceed chosen limiting values. Other standards can be used as long as they are effective in eliminating pads that are not sufficiently effective in reducing applied forces.
6. The preferred manikin impacts described here proceed through a stiff spring in order to simulate a realistic impact. An alternative method consists of attaching an elastic member to the bottom of the projectile. Other types, placements, and shapes of intermediary elastic elements are possible as long as they give rise to such realistic impacts.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A testing or measuring method comprising:
   providing a projectile apparatus comprising:
   a frame,
   at least one rod or rail supported by said frame in an at least partially vertical orientation,
   a projectile of predetermined mass or weight slidably mounted to said at least one rod or rail, and
   an elastic impact member disposed relative to said at least one rod or rail and said projectile so as to be disposed at a lower end of said at least one rod or rail so that said projectile impacts on said elastic impact member upon a falling of said projectile along said at least one rod or rail;
   placing a protective sports device on a manikin part so as to simulate a person's use of said protective sports device;
   operating said projectile apparatus to impact said elastic impact member and indirectly impact said protective sports device via said elastic impact member, at a predetermined location on said protective sports device and concomitantly over said manikin part, with said projectile having a predetermined or prescribed velocity; and
   during the impacting of said projectile on said elastic impact member and indirectly on said protective sports device via said elastic impact member, operating one or more sensors to measure respective forces exerted by the impact on at least one of said protective sports device and said manikin part.

2. The method defined in claim 1 wherein said one or more sensors are positioned to measure forces at locations taken from the group consisting of an external surface of said protective sports device, a lower side of said projectile, and between said protective sports device and said manikin part.

3. The method defined in claim 2, further comprising placing at least one of said sensors at a predetermined position between said protective sports device and said manikin part.

4. The method defined in claim 2, further comprising connecting said one or more sensors to an electronic signal processor and operating said signal processor to compute at least one measure of effectiveness of said protective sports device, said measure being computed in accordance with an algorithm taken from the group consisting of:

$$(1/T) \times \int_0^T f(t)dt \quad \text{(i)}$$

which represents an average of the applied force f(t) over the duration T of the impact;
(ii) an algorithm determining the sum of the maximum forces measured on each sensor under the pad; and
(iii) the ratio e=v'/v of the rebound load speed v' and the incident load speed v.

5. The method defined in claim 4, further comprising computing at least one metric defined as the difference between said at least one measure of effectiveness measured when said protective sports device is in place and the same measure of effectiveness measured for identical impacts directly on said manikin part, without said protective sports device in place.

6. The method defined in claim 5, further comprising using said at least one metric to define a performance standard for protective equipment by requiring that said at least one metric measured for the equipment lies in a specified range.

7. The method defined in, claim 1 wherein said elastic impact member has predetermined elastic and damping properties, said predetermined mass or weight and said predetermined or prescribed velocity and said properties of said elastic member being selected so that impact forces exerted approximate those encountered in a contact sport in which said protective device is used.

8. The method defined in claim 1 wherein said elastic impact member is a spring.

9. The method defined in claim 1 wherein the operating of said projectile apparatus includes releasing said projectile from a predetermined height above said protective sports device and said manikin part.

10. The method defined in claim 1 wherein said protective sports device is taken from the group consisting of a shoulder pad, a shin guard and a helmet.

11. The method defined in claim 1 wherein said manikin part includes a hard shell surrounding a polymeric filling material.

12. The method defined in claim 1 wherein said elastic impact member is positionable at a predetermined location on said protective sports device over said manikin part for receiving said projectile during an impact of said projectile and transmitting said impact onto said protective sports device, further comprising a holder having a recess and a rounded bottom, said holder being disposable on said protective sports device at said predetermined location, said elastic member having a lower end positionable inside said recess.

13. A testing or measuring assembly comprising:
a frame;
at least one rod or rail supported by said frame in an at least partially vertical orientation;
a mass or weight slidably mounted to said at least one rod or rail;
an elastic impact member disposed relative to said at least one rod or rail and said mass or weight so as to be disposed at a lower end of said at least one rod or rail so that said mass or weight impacts on said elastic impact member upon a falling of said mass or weight along said at least one rod or rail; and
at least one force sensor disposable at a location taken from the groin consisting of an upper or external surface of a protective sports device, a lower side of said projectile, and between said protective sports device and said manikin part.

14. The assembly defined in claim 13 wherein said at least one force or acceleration sensor is attached to said projectile.

15. The assembly defined in claim 13 wherein said at least one force sensor is one of a plurality of force sensors each disposable at a location taken from the group consisting of said upper or external surface of said protective sports device, said lower side of said projectile, and between said protective sports device and said manikin part.

16. The assembly defined in claim 15, further comprising an electronic signal processor operatively connected to said sensors and configured to record output signals of said force sensors as functions of time.

17. The assembly defined in claim 16 wherein said signal processor is further configured to compute at least one measure of effectiveness of said protective sports device, said measure being computed in accordance with an algorithm taken from the group consisting of:

$$(1/T) \times \int_0^T f(t)dt \quad \text{(i)}$$

which represents an average of the applied force f(t) over the duration T of the impact;
(ii) an algorithm determining the sum of the maximum forces measured on each sensor under the pad; and
(iii) the ratio e=v'/v of the rebound load speed v' and the incident load speed v.

18. The assembly defined in claim 16 wherein said signal processor is further configured to compute at least one measure of effectiveness of said protective sports device, said measure being computed in accordance with an algorithm taken from a first group consisting of:
(i) an algorithm determining a maximum recorded acceleration and force;

$$SI = \int_0^{t0} a(t)^p dt \quad \text{(ii)}$$

where SI, standing for "Severity Index," is the integral of acceleration a(t) of the impacting projectile, raised to power p, over the duration of the impact and where a(t) is acceleration as recorded on an accelerometer attached to the impacting weight w, at time t during the impact, and where f(t)=w*a(t) is the corresponding force;

$$(1/T) \times \int_0^T f(t)dt \quad \text{(iii)}$$

which represents an average of the applied force f(t) over the duration T of the impact;
(iv) an algorithm determining maximum and average forces measured on each sensor under the pad;
(v) an algorithm determining the sum of the maximum forces measured on each sensor under the pad; and
(vi) the ratio e=v'/v of the rebound load speed v' and the incident load speed v,
said signal processor being further configured to compute at least one measure of effectiveness of said protective sports device, said measure being computed in accordance with an algorithm taken from a second group defined as the differences between the metrics of said first group measured when a protective equipment is in place and the same metrics measured for identical impacts when a protective pad is not in place.

19. The assembly defined in claim 13 wherein said elastic impact member is a helical spring, said spring having a lower end positioned inside a recess and an upper end surrounding a lower end portion of said rod or rail.

20. A testing or measuring assembly comprising:
a frame;
at least one rod or rail supported by said frame in an at least partially vertical orientation;
a mass or weight slidably mounted to said at least one rod or rail;
an elastic impact member disposed relative to said at least one rod or rail and said mass or weight so as to be disposed at a lower end of said at least one rod or rail so that said mass or weight impacts on said elastic impact member upon a falling of said mass or weight along said at least one rod or rail; and
a manikin part for temporary attachment to a protective sports device in simulation of a user's wearing the protective sports device, wherein said elastic impact member is positionable at a predetermined location on said protective sports device over said manikin part for receiving said mass or weight during an impact of said mass or weight and transmitting said impact onto said protective sports device.

21. The assembly defined in claim 20, further comprising a holder having a recess, said holder being disposable on said protective sports device at said predetermined location, said elastic member having a lower end positionable inside said recess.

22. The assembly defined in claim 21 wherein said holder has a rounded bottom.

* * * * *